(12) United States Patent
Vlachomitrou et al.

(10) Patent No.: US 11,903,748 B2
(45) Date of Patent: Feb. 20, 2024

(54) METHOD AND DEVICE FOR CREATING A CEPHALOMETRIC IMAGE

(71) Applicant: CARESTREAM DENTAL LLC, Atlanta, GA (US)

(72) Inventors: Anna-Sesilia Vlachomitrou, Rochester, NY (US); Vincent Loustauneau, Fontenay sous Bois (FR); Michael D. Heath, Rochester, NY (US); Jean-Marc Inglese, Bussy-Saint-Georges (FR)

( * ) Notice: Subject to any disclaimer, the term of this patent is extended or adjusted under 35 U.S.C. 154(b) by 162 days.

(21) Appl. No.: 17/203,201

(22) Filed: Mar. 16, 2021

(65) Prior Publication Data

US 2022/0054095 A1  Feb. 24, 2022

Related U.S. Application Data

(63) Continuation of application No. 16/065,801, filed as application No. PCT/US2015/000478 on Dec. 23, 2015, now abandoned.

(51) Int. Cl.
*A61B 6/02* (2006.01)
*A61B 6/14* (2006.01)
*A61B 6/00* (2006.01)

(52) U.S. Cl.
CPC ............... *A61B 6/025* (2013.01); *A61B 6/14* (2013.01); *A61B 6/5205* (2013.01)

(58) Field of Classification Search
CPC .......... A61B 6/025; A61B 6/14; A61B 6/5205
See application file for complete search history.

(56) References Cited

U.S. PATENT DOCUMENTS

2009/0041191 A1* 2/2009 Suzuki ................ A61B 6/488
378/98.5
2010/0034340 A1* 2/2010 Spartiotis ............ A61B 6/588
378/4

* cited by examiner

*Primary Examiner* — Christine S. Kim

(57) ABSTRACT

Extra-oral dental method and/or apparatus embodiments according to this application can generate cephalometric imaged by digital tomosynthesis. An extra-oral dental imaging system embodiment for creating a cephalometric image of at least part of a human skull can include an X-ray source, an imaging device suitable for producing multiple frames during at least part of an exposure; a memory for registering and/or storing said multiple frames; and a manipulator for displacing the imaging device along an exposure profile between multiple frames during said at least part of the exposure of said object. The imaging device has an active area having a long dimension m and a short dimension n, wherein the aspect ratio m:n is strictly inferior to 1.5.

22 Claims, 6 Drawing Sheets

METHOD AND DEVICE FOR CREATING A CEPHALOMETRIC IMAGE

FIELD OF THE INVENTION

The present invention concerns a method for creating a cephalometric image as well as a related system.

The present invention relates to the field of dental extra-oral imaging systems.

More specifically, the present invention relates to cephalometric imaging, namely a linear projection of the human skull or part of the human skull.

BACKGROUND

A 2D cephalometric radiograph is a medical imaging technique comprising the linear projection of a human head on a flat 2D sensor (or, in more general terms, an imaging layer of an imaging device).

Cephalometric analysis is a technique commonly employed by orthodontists, dentists, et al. to analyze the dimensional relationships in the craniofacial complex, to predict future changes, to assess the effect of ongoing treatment plans, to evaluate the patient's dentomaxillofacial proportions, and to aid in the diagnosis of abnormalities and asymmetries.

Consequently, there is a need for a system which produces high-resolution cephalometric images.

A planar imaging system has two types of resolution: an in-plane spatial resolution, in the direction parallel to the imaging layer of the imaging device; and a depth resolution, perpendicular to the imaging layer of the imaging device.

The image depth resolution depends primarily on the width of the sensor along the direction of movement and the actual movement trajectory.

In the known extra-oral systems for performing panoramic imaging, the sensor is typically narrow in aspect, long and with a small width. In order to obtain a linear projection of the entire human skull (cephalometric image), the imaging system includes a cephalometric or "ceph" arm: the panoramic sensor is attached to the "ceph" arm in the cases where a cephalometric image is needed.

As a consequence, there is a large separation provided between the X-ray source and the sensor in order to minimize distortions and magnification disproportions in the projected image. Such a cephalometric arm is cumbersome. Moreover, this technique creates a cephalometric image where both the left and right sides of the patient's cranium are superimposed with differing magnifications, which can result in image distortion and may be of limited diagnostic and therapeutic utility.

The document U.S. Pat. No. 8,306,181 discloses an extra-oral dental imaging system with a sensor capable of producing a cephalometric image without the use of an additional "ceph" arm.

A linear sensor is used with an aspect ratio m:n superior to 1.5, wherein m is the long dimension of the active area of the sensor and n is the short dimension of the active area of the sensor.

The sensor and the X-ray source are displaced together along a trajectory divided into three segments: a first exposure, a non-radiating movement and a second exposure. During the two exposure segments, the left and right side of the skull are imaged.

The two segments of the profile during which the skull is exposed to radiation are substantially linear. The length of the linear exposure is generally more than 5 cm, but in any case long enough to produce data that can be used to produce a volumetric reconstruction of an image to be displayed.

The distance between the focal point of the X-ray source and the imaging device is small compared to the standard case with the "ceph" arm.

After the exposures, a volumetric reconstruction algorithm is used to calculate vertical slices along the imaging direction. The content of each individual slice is reconstructed using tomosynthesis techniques. The vertical slices are then transformed to eliminate different magnification factors of different vertical slices, and then added together to produce a 2D cephalometric image.

However, due to the use of a linear sensor with a small width, the voxels in the volumetric image provided by the sensor have a small size in the imaging dimension, and thus a high spatial resolution, but a large size in the perpendicular dimension, and thus a poor depth resolution.

The present invention aims to address, in whole or in part, at least the foregoing and other deficiencies in the related art.

SUMMARY OF THE INVENTION

According to one aspect of the disclosure, there is provided a method for creating a cephalometric image of at least part of a human skull in an extra oral dental imaging system, such system comprising: an X-ray source for irradiating an object to be imaged; an imaging device suitable for producing multiple frames during at least part of an exposure of said object; a manipulator for displacing the imaging device along an exposure profile between multiple frames during said at least part of the exposure of said object, the manipulator permitting the movement of the X-ray source and the imaging device by means of selective translation and selective rotation.

According to the invention, the method comprises the following steps:

setting said imaging device with an active area having a long dimension m and a short dimension n, wherein the aspect ratio m:n is strictly inferior to 1.5;

synchronously displacing the X-ray source and the imaging device along said exposure profile, said exposure profile comprising at least one substantially linear section wherein said X-ray source and said imaging device are translated while rotating in the same direction; and registering said multiple frames produced by the imaging device during the exposure of said object to be imaged.

Due to the use of an imaging device with a quite large active area—by which it is meant the area of the sensor which is both irradiated and participates in image construction—combined with a linear displacement during the exposure of the object to be imaged, a high depth resolution can be achieved. The multiple frames produced by the imaging device may be used for reconstructing volumetric data thanks to the high depth resolution obtained in a direction perpendicular to the plane of the image.

Thus, thanks to the 3D information, an accurate landmarking may be generated and precise reference points may be used for the cephalometric analysis.

In a possible embodiment, the at least one substantially linear section of the exposure profile is oriented almost parallel to a mid-sagittal plane or a coronal plane, or angled to said mid-sagittal plane.

Exposure profiles so oriented will produce lateral, frontal, and oblique cephalometric images, thereby maximizing the utility and flexibility of the method.

Preferably, the exposure profile comprises at least two separate substantially linear sections at two opposite angular extremes about the object to be imaged.

This is advantageous in that the object to be imaged is effectively scanned from two opposite sides. In this way, bilateral images may be created, for instance of a patient from the left and right sides, thereby improving the quality and utility of the resulting image.

Most preferably, the short dimension n of the active area of the imaging device extends along said at least one substantially linear section during the exposure of said object.

In this way, the depth resolution of the resulting image is maximized.

In a preferred embodiment, the angular range of the rotational movement of the imaging device and the X-ray source is at least equal to 15°, and preferably equal to 30°.

This is advantageous in that the size of the imaging machine can be minimized while still providing a high-resolution imaging.

Preferably, the X-ray source is displaced along a trajectory having a curvature directed towards said object, and the imaging device is displaced along a trajectory having a curvature directed away from said object.

This is advantageous in that it will give a higher depth resolution in the images so generated than where the trajectories are linear, or have an opposite curvature.

Preferably, the length of said at least one substantially linear section is comprised between 70 and 250 mm.

This is advantageous in that such dimensions strike an acceptable balance between image quality, patient X-ray dose, and overall apparatus size.

Preferably, the aspect ratio m:n is inferior to 1.3, and most preferably inferior to 1.2.

This is advantageous in that a method utilizing an imaging device with an active area so dimensioned will realize greater depth resolution than those methods known in the art.

In a possible embodiment, the long dimension m of said active area is equal to 140 mm and the short dimension n of said active area is equal to 120 mm.

An imaging method utilizing an active area so configured will realize an advantageous combination of high image resolution, low patient X-ray dosage, and equipment compactness.

In another possible embodiment, the long dimension m of said active area is equal to 210 mm and the short dimension n of said active area is equal to 120 mm.

Such a sensor will yield images of maximal quality and resolution.

In another possible embodiment, the method further comprises a step of computing the multiple frames produced during at least one part of the exposure by a shift-and-add processing, thereby reconstructing at least one slice; or by a volumetric approach, thereby reconstructing a three-dimensional volume and subsequently extracting at least one slice from said volume; said at least one slice from said volume containing in-focus imaging data belonging respectively to at least one depth of said object to be imaged.

In this way, a three-dimensional model of the patient's anatomy is constructed, providing high-resolution, high-precision information that is not limited to a narrow "focal trough" but is rather of a consistently high quality through the entire depth of the scan.

Moreover, from this model, high-quality simulations of conventional imaging scans can easily be extracted and/or extrapolated, maximizing the diagnostic and therapeutic utility of each scan.

In possible embodiments, the volumetric approach is selected from a Statistical Algebraic Reconstruction Technique (SART), a Statistical Iterative Reconstruction Technique (SIRT), or a Filtered Back Projection Technique.

Such approaches are advantageous in that they yield a high-quality reconstruction of the subject while limiting the X-ray dosage incurred. In particular, certain a priori information is employed so as to refine the reconstruction, such as the positions of certain anatomical features in the patient's cranium. This in turn refines the reconstruction and improves the quality of the images produced from it.

Preferably, the method further comprises a step of using each reconstructed slice for the extraction of cephalometric features.

Most preferably, in a step of automatic cephalometric tracing, said extracted cephalometric features of each slice are put together.

In this way, a complete cephalometric image is constructed, thereby enabling e.g. a dentist to perform diagnostic and therapeutic procedures based thereupon.

In a possible variant embodiment, said several slices are reconstructed and combined to give a separate linear projection for the left and right sides of said object to be imaged.

In this way, a pair of cephalometric images is constructed with a single scan, reducing X-ray dosage to the patient while providing bilateral cephalometric information.

In another possible variant embodiment, said several slices are reconstructed and retro-projected to a distance superior to 1.50 meters, and preferably superior to 4 meters, on a cone beam or parallel geometry so as to create a synthesized 2D cephalogram of the skull.

This is advantageous in that a traditional 2D cephalogram is produced, without requiring an extra "ceph arm" or the space to accommodate it, or any additional X-ray exposure to the patient.

According to another aspect of the disclosure, there is provided an extra-oral dental imaging system for creating a cephalometric image of at least part of a human skull, such system comprising:
  an X-ray source for irradiating an object to be imaged;
  an imaging device suitable for producing multiple frames during at least part of an exposure of said object;
  a manipulator for displacing the imaging device along an exposure profile between multiple frames during said at least part of the exposure of said object, the manipulator permitting the movement of the X-ray source and the imaging device by means of selective translation and selective rotation.

According to the invention, said imaging device has an active area having a long dimension m and a short dimension n, wherein the aspect ratio m:n is strictly inferior to 1.5; said manipulator synchronously displaces the X-ray source and the imaging device along said exposure profile, said exposure profile comprising at least one substantially linear section wherein said X-ray source and said imaging device are translated while rotating in the same direction; and said system comprises a memory for registering said multiple frames produced by the imaging device during the exposure of said object to be imaged.

BRIEF DESCRIPTION OF THE DRAWINGS

The foregoing and other objects, features and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationship or principles of the invention. Some conventional components that would be needed for implementation of the described embodiments, such as support components used for providing power, for packaging, and for mounting and protecting x-ray system components, for example, are not shown in the drawings in order to simplify the description.

DESCRIPTION OF EXEMPLARY EMBODIMENTS

Where they are used, the terms "first", "second", and so on, do not necessarily denote any ordinal or priority relation, but may be used for more clearly distinguishing one element or time interval from another. The term "exemplary" indicates that the description is used as an example, rather than implying that it is an ideal.

Figure 1A:
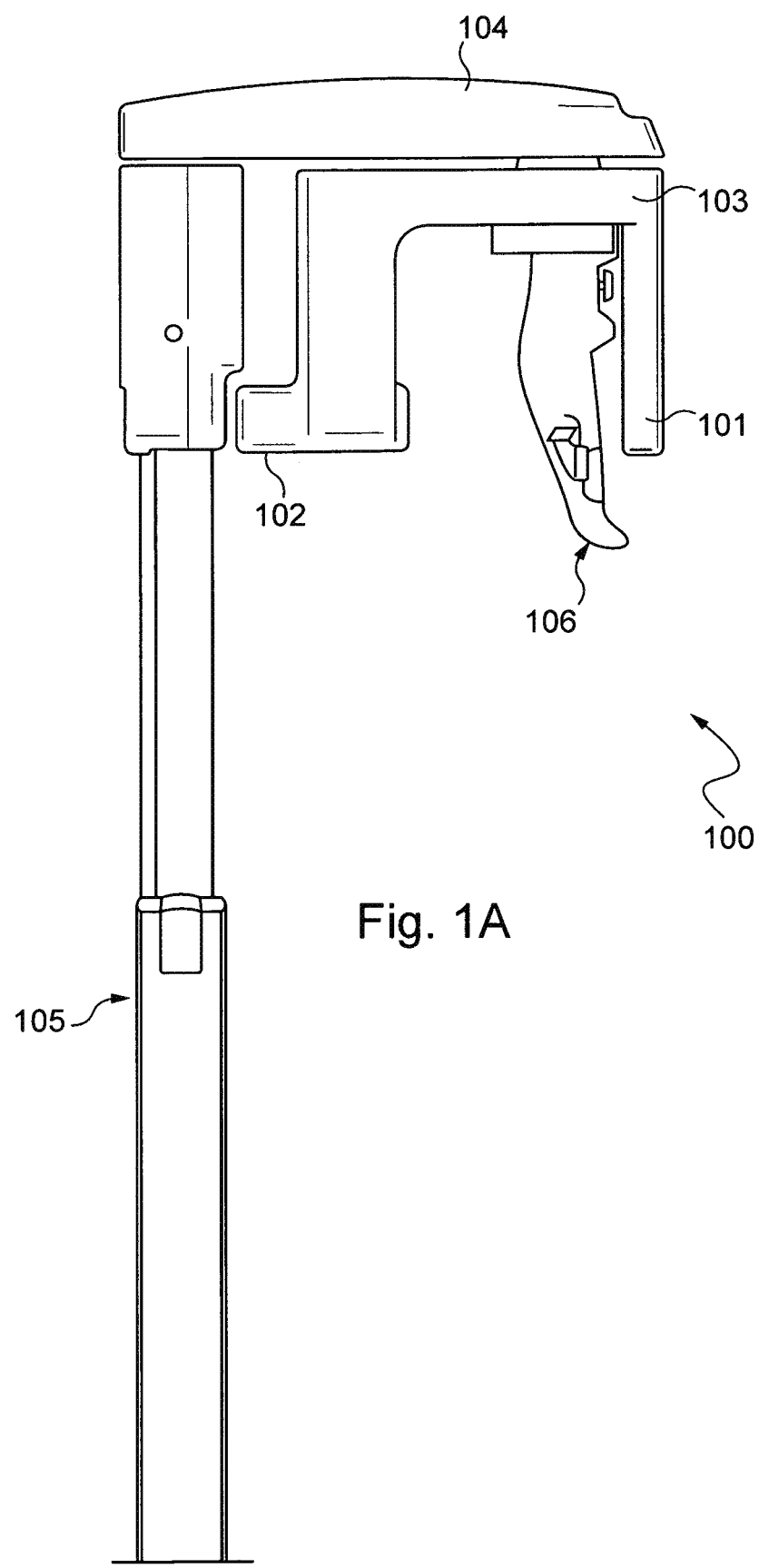
FIG. 1A is a diagram showing a perspective view of an extra-oral dental imaging system according to a first embodiment of the invention.

FIG. 1A illustrates the general configuration of an extra-oral dental imaging system 100 according to a first embodiment of the invention. The imaging system 100 comprises a sensor 101 and an X-ray source 102. The sensor 101 and the X-ray source 102 are mounted in this embodiment on a gantry 103 which is itself fastened to a horizontal mount 104.

The horizontal mount 104 is fixed to a vertical column 105 which may comprise classical telescopic means not disclosed here below, permitting to set the height of the imaging system.

The imaging system also comprises a patient holder 106 which maintains the patient head in a defined and fixed position under the gantry 103, between the X-ray source 102 and the sensor 101 during the imaging process.

The patient holder 106 may be similar to a patient holder used, in prior art, on a cephalometric imaging arm to maintain the patient head during the exposure.

Figure 1B:
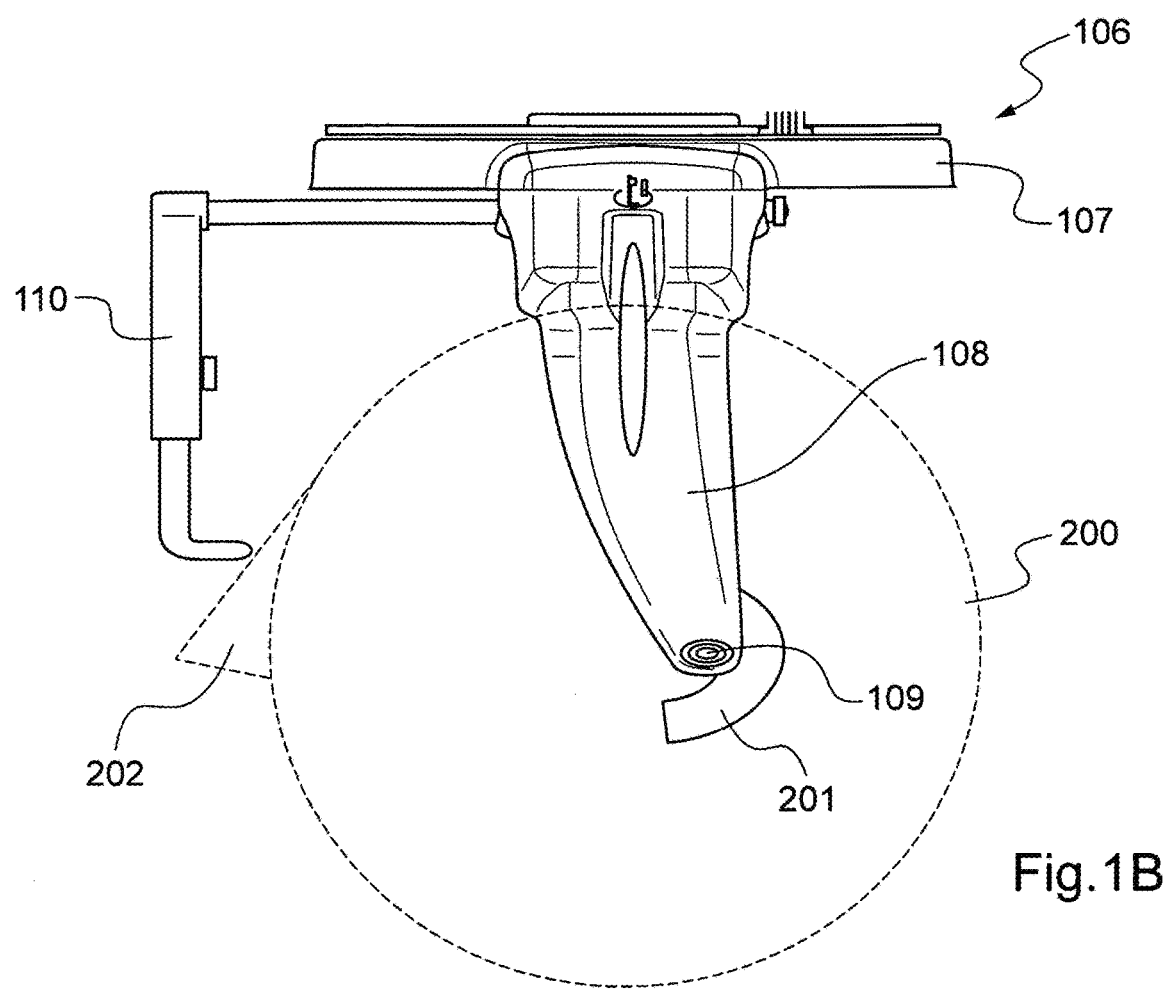
FIG. 1B is a detail of an alternate configuration of a patient support for the imaging system of FIG. 1A.

As an alternative embodiment, the patient holder 106 may be composed of two ear rod holders 108 supporting two ear rods 109 to be inserted in the patient's ear canals 201, as illustrated in FIG. 1B. The two ear rod holders are symmetrically slideable on each side to adjust to the width of the patient's head 200.

A nosepiece 110 is adjustable in the horizontal and vertical directions to be positioned exactly at the bridge (nasion) of the patient's nose 202. The ear rods 109 inserted into the ear canals 201 of the patient block any possible movement of the patient's head, except the rotation of the head about an axis passing through the two ear rods 109.

The nosepiece 110 thus serves to prevent such movement, constraining the patient's movement in this last degree of freedom. A mount 107 supports the ear rod supports 108 and the nosepiece 110, and can be fitted on the mount 104 of the imaging device through the gantry 103.

In an alternative embodiment, the patient holder 106 can be fixed with an arm (not represented on the vertical column 105); this will allow, in certain situation, a greater deal of freedom in the configuration and operation of the imaging system.

The X-ray source 102 is adapted to irradiate the object to be imaged, and in this embodiment, at least a part of a human skull for creating a cephalometric image.

The sensor 101 forms an imaging device suitable for producing multiple frames during the exposure of the object to be imaged.

In one embodiment, it is envisioned that the X-ray sensor 101 is a charge-coupled device (CCD), a CMOS sensor, or a TFT sensor, as such a device could be easily integrated into a computerized imaging system with minimal adaptation.

The gantry 103 forms a manipulator for displacing the sensor 101 and the X-ray source 102 along an exposure profile.

Thus, the manipulator or gantry 103 permits the movement of the X-ray source 102 and the sensor 101 by means of a selective translation and a selective rotation.

Figure 1C:
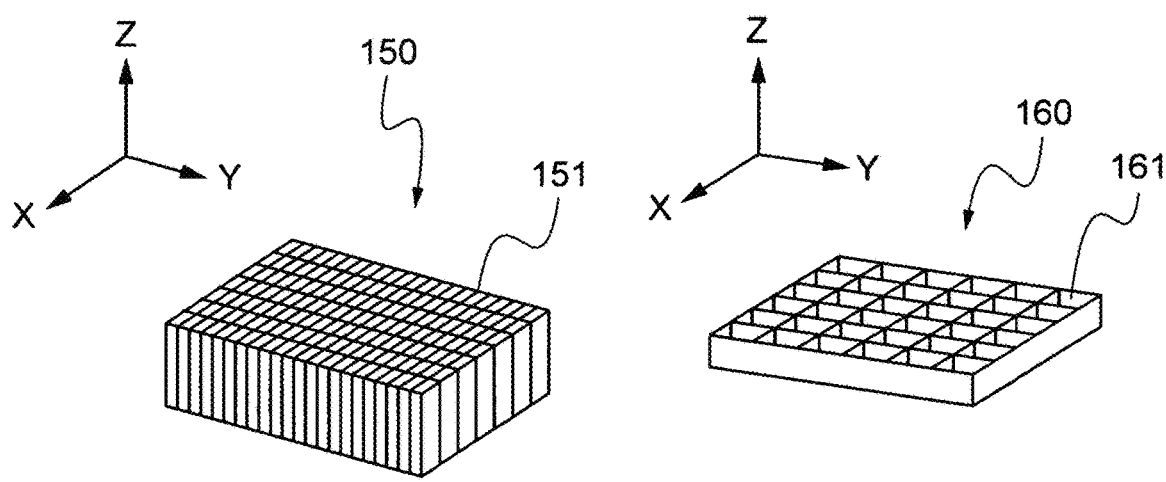
FIG. 1C is a representation of the voxel size and shape realized by the method of the invention and a scan according to a CBCT method of the art.

FIG. 1C illustrates the result of the invention as compared to that of a Cone-Beam Computerized Tomography (CBCT) technique as known in the art. The grid 150 is a representation of the result of the method of the present invention, while the grid 160 is representative of the result of the CBCT method. In particular, it can be seen that the area in the x-y plane of each of the "blocks" 151 is very small compared to the blocks 161, meaning that the in-plane resolution of the method according to the present invention is very high compared to that of the CBCT method.

On the other hand, the depth resolution is not as fine (as can be seen in the increased height of the grid 150 relative to the grid 160). However, for cephalometric purposes the depth resolution of the method of the present invention is nonetheless acceptable, and the x-ray dosage remains very low compared to CBCT.

Figure 2:
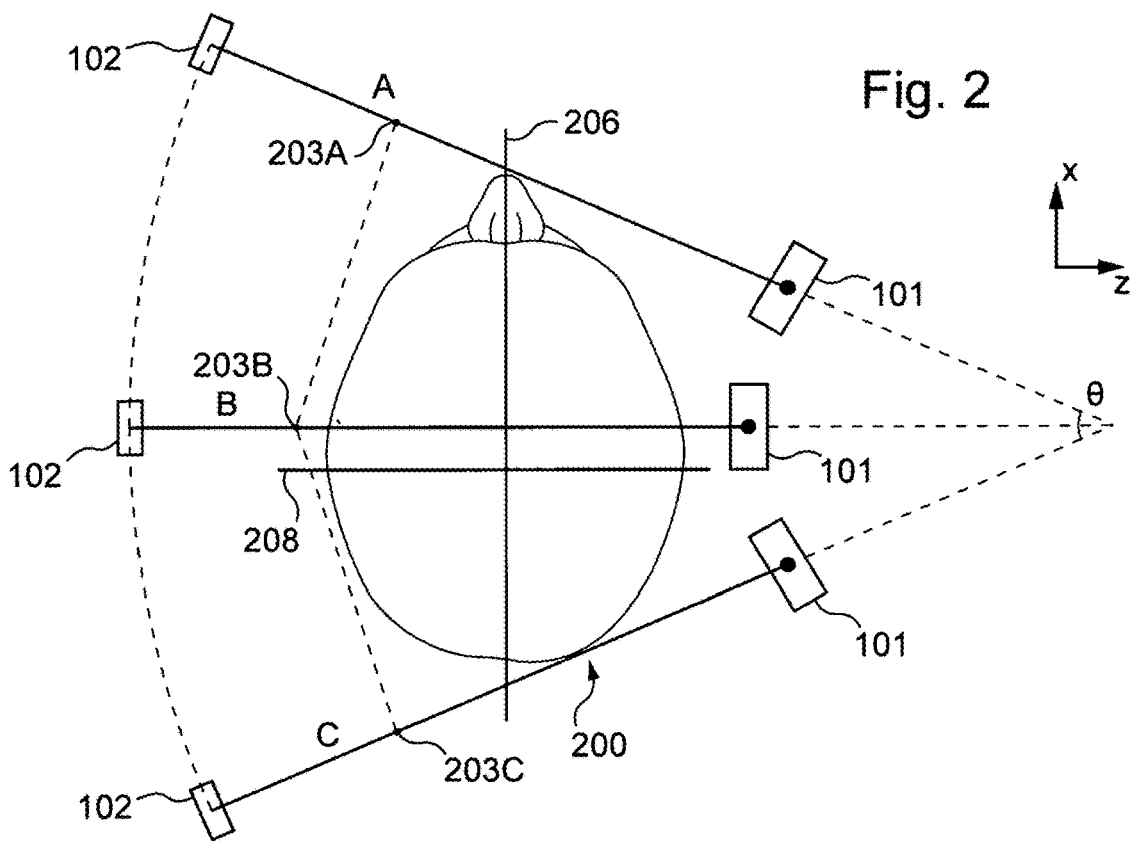
FIG. 2 is a diagram showing an exemplary exposure profile performed in a method for creating a cephalometric image according to a first embodiment of the invention.

Turning now to FIG. 2, one exposure profile of the imaging system 100 is illustrated in greater detail.

The exposure profile is performed for instance when creating a cephalometric image of a part of human skull.

During the exposure of the patient 200, the X-ray sensor 101 is suitable for producing multiple frames.

As known in an extra-oral dental imaging system, it comprises a memory for registering the frames produced by the imaging device.

In this embodiment, the imaging system comprises a memory for registering the multiple frames produced by the X-ray sensor 101 during the exposure of the patient skull.

The imaging system 100 is first positioned about a patient 200, such that the sensor 101 and the X-ray source 102 are disposed in an initial position A. The initial position A of the X-ray sensor 101 and the X-ray source 102 are such that a line drawn between them lies just forward of the face of the patient 200.

The X-ray sensor 101 and the X-ray source 102 are swept past the patient 200 as displayed in FIG. 2; more specifically, the X-ray sensor 101 and the X-ray source 102 are shown in the initial position A mentioned above, a final position C, and an intermediate position B between the initial position A and the final position C.

The effect of this displacement is twofold: the X-ray sensor 101 and the X-ray source 102 are rotated through an angle θ, while simultaneously translating along an X-axis from the initial position A to the end position C.

Thus, the X-ray source 102 and the X-ray sensor 101 are synchronously displaced along the exposure profile as depicted in FIG. 2. The exposure profile comprises at least one substantially linear section between the initial position A and the end position C.

As illustrated in FIG. 2, the X-ray source 102 and the X-ray sensor 101 are translated while rotating in the same direction. The angular range θ of the rotational movement of the sensor 101 and the X-ray source 102 is at least equal to 15°, and preferably equal to 30°.

In this way, thanks to the limited rotation of the sensor 101 and the X-ray source 102, the profile of the patient is irradiated and imaged with an almost perpendicular angular incidence; the curvature of the trajectory of the x-ray source 102 and the x-ray sensor 101 are exaggerated here for illustrative purposes. The trajectory of the gantry can be considered in gross as being a substantially linear path, in that the rotation of the gantry is small or minimal relative to its translation.

As can be seen in FIG. 2, the patient is positioned close to the sensor 101, so that the distance between the sensor 101 and the patient 200 is lower than the distance between the patient 200 and the x-ray source 102. This limits the distortion of the image due to the conical shape of the x-ray beam emitted by the x-ray source 102.

The curvature of the trajectory of the x-ray source 102 is directed towards the patient 200, and the curvature of the trajectory of the sensor 101 is directed away from the patient. There thus exists an instantaneous center of rotation that is located on the other side of the sensor 101 from the x-ray source 102. As the patient 200 is located close to the sensor 101, the distance between the patient and the instantaneous center of rotation is minimized when the instantaneous center of rotation is on the side of the sensor 101, as illustrated in FIG. 2, resulting in a higher depth resolution.

For any volume element (voxel) position, it is ideal that the average directions of all rays passing through said position to match as closely as possible the ray direction of a true 2D cephalometric image, i.e. that which would be produced by an apparatus with the sensor placed at the end of the long "ceph arm" described above. This in turn means that the tomosynthesis blur function will have reduced or minimal magnification and distortion artifacts.

This top view of the system does not show the path of the x-rays in the Z-direction. The average ray direction of CBCT x-rays will have a Z-component whose magnitude increases with distance from the primary plane. This means that the blur (associated with the limited tomosynthetic depth resolution) will "smear" anatomic features in a direction other than the ray direction of true two-dimensional cephalometric rays. The direction of this smear will align less closely with the true (and desired) 2D cephalometric ray direction as the rays pass through anatomy that is further form the plane and closer to the head and neck of the patient. Without highly accurate (i.e. fine) depth resolution, this will lead to blurring in a simulated cephalometric reprojection of the data outside of a very thin focal trough.

In the CBCT process, this depth resolution is created from the information captured by multiple x-ray beam paths through each voxel from the CBCT projections. If the sensor 101 were very large such that the entire head, or nearly the entire head, were captured in each projection, there would be a lot of flexibility allowed in the sequence of projections and the capture geometry used. The medium-sized sensor 101 of the apparatus 100 limits the geometry of the capture as subsections of the anatomy must be captured with each projection and then combined by image-processing methods to "stitch" together the image of the entire head.

In the present invention, however, rotation through the scan tilts the sensor 101 so that it is not contained within a single plane. A center of rotation 203 (numbered here as 203A, 203B, and 203C to correspond to the three positions A, B, and C of the gantry 103) is moved with an X component (along the sagittal plane of the patient 200). The center of rotation 203, in addition to moving in the X-direction (i.e. the sagittal direction), also moves a much smaller amount in the Z-direction (i.e. the coronal direction) in the case of a cephalometric scan as depicted in FIG. 2. Moreover, the center of rotation 203 is positioned above the patient's head 200 and on the same side of the X-ray source 102 (in FIG. 2, the left-hand side).

The general "convex" scan path illustrated in FIG. 2 balances all of these requirements. The exact scan path will depend, of course, on the system components and imaging requirements, such as any constraints on the movement of the center of rotation, the size of the sensor 101, and the size requirements and constraints placed upon the system by patient anatomy.

More precisely, the sensor 101 and the X-ray source 102 are aligned in front of each other according to a direction substantially parallel to the coronal direction 208, and thus perpendicular to the mid-sagittal plane 206.

Moreover, the length of the substantially linear section is comprised between 70 and 250 mm. In a general way, the length is sufficient to sweep the whole profile of the patient skull. The speed of the translation of the gantry 103 is typically about 4 centimeters per second and the capture frame rate is comprised between 15 and 50 frames per second, most preferably between 15 and 30 frames per second.

High capture frame rates are generally preferable for high depth resolution; however, since the sensor 101 has a large active area and realizes a fine depth resolution, this makes it possible to use a lower frame rate than what might be employed in the art to reduce the amount of raw image data generated, thereby minimizing image-processing computing loads while still maintaining good depth resolution in reconstructed images.

Of course, it will be recognized that the exposure profile may be performed in a direction opposite from that illustrated in FIG. 2 without any substantial effect on the accuracy or resolution of the imaging process.

Thus the almost linear exposure profile through the mid-sagittal direction can provide a lateral cephalogram of the skull of the patient 200.

Of course, the exposure profile depicted in FIG. 2 is only a way of example: a substantially linear exposure profile through the coronal direction can provide a frontal cephalogram and a substantially linear exposure profile through a plane angled compared to the sagittal direction can provide a tilted cephalogram.

Figure 3:
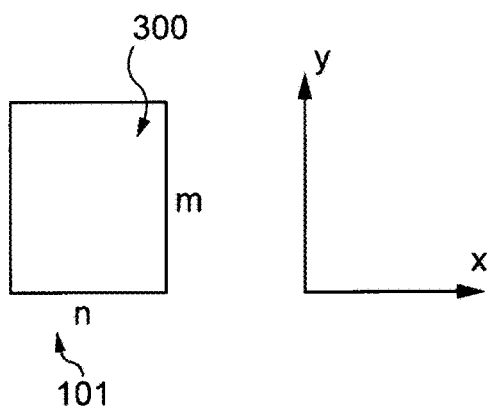
FIG. 3 is a diagram showing an exemplary active area of an imaging device provided in the method for performing a cephalometric image according to the first embodiment of the invention.

FIG. 3 gives more detail on the configuration of the X-ray sensor 101. The X-ray sensor 101 comprises an active sensor surface or active area 300, having a width n and a height m.

As displayed in FIG. 3, the height m of the active area 300 extends along a direction Y and the width n extends along a direction X corresponding to the substantially linear direction of the exposure profile as depicted in FIG. 2.

It will be noted that the aspect ratio of the active sensor surface 300 is close to square, unlike the scanning systems known in the art which employ sensors having a very high aspect ratio (i.e. being very tall and thin).

Thus, the ratio m:n is strictly inferior to 1.5. Ideally, the aspect ratio m:n is inferior to 1.3, and most ideally below 1.2.

In the particular embodiment here envisioned, the active sensor surface 300 has dimensions of 140 mm×120 mm, yielding an aspect ratio of approximately 1.17. Of course, it may be contemplated that these dimensions may vary according to the particular embodiment in question.

In such an X-ray sensor 101, the spatial resolution (corresponding the in plane voxel size) usually reflects the sensor pixel size. As an example, the spatial resolution is around 100-200 µm, depending on the pixel size of the X-ray sensor 101.

The depth resolution, corresponding to the slice separation, depends on the trajectory, angular span and sensor size. In the present embodiment, the depth resolution has values generally between 0.5 mm and 1 mm.

A depth resolution of 0.5 to 1 mm gives measurements close to real 3D measurements.

Even if the depth resolution is superior to 1 mm, since the spatial resolution is very high, it give the possibility to distinguish easily the in focus from the out of focus structures in the multiple frames produced by the X-ray sensor 101 during the exposure of the object to be imaged.

In this way, the coordinates of a cephalometric point in the space (defined by the axis X, Y, Z) are given with a high precision and for an example with only 1% error compared to real 3D measurements.

Figure 4:
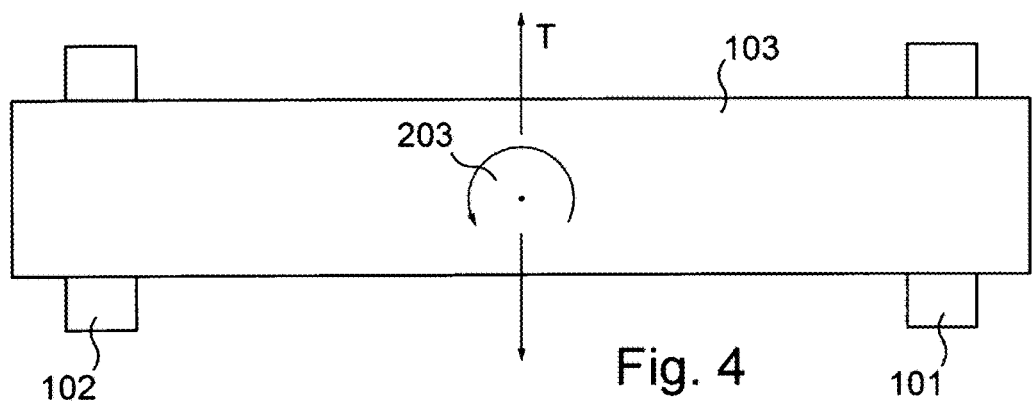
FIG. 4 is an exemplary configuration for a gantry of the imaging system of FIG. 1A.

FIG. 4 illustrates an exemplary configuration for the gantry 103 adapted to displace the X-ray sensor 101 and the X-ray source 102 along the exposure profile previously described.

The gantry 103 is configured to translate laterally along the direction T, as well as to rotate about a central axis of rotation 203. In this embodiment, the gantry 103 is mounted to the horizontal mount 104 through translation and rotation means in order to be able to translate and rotate around the patient 200. For example, in order to perform the exposure profile as depicted in FIG. 2, the gantry 103 comprise a translation mechanism configured to synchronously move the X-ray source 102 and the sensor 101. In one embodiment, the translation mechanism is adapted to translate the gantry 103 with regard to the horizontal mount 104 along the length of the profile exposure.

For example, in order to get a lateral cephalogram, the gantry 103 is translated with the X-ray source 102 and the sensor 101 according to the direction T parallel to the sagittal direction.

This rotation has a range which corresponds to the sweep angle θ as illustrated in FIG. 2.

To obtain the specific exposure profile, the rotation of the X-ray sensor 101 and the X-ray source 102 and the translation of the gantry 103 are synchronously regulated, for example by controlling means.

The controlling means in an extra-oral dental imaging system, used to control the displacement of the gantry 103 and of the X-ray sensor 101 and the X-ray source 102 are known and will not be described in more details.

In this way, a great deal of control of the incidence of the X-ray beam passing between the X-ray source 102 and the X-ray sensor 101, relative to the patient 200, is achieved. More specifically, the point at which the X-ray beam emitted by the X-ray source 102 is incident upon the patient, as well as the angle of said beam relative to the mid-sagittal plane 206 and/or coronal plane 208 (depicted in FIG. 2) can be readily controlled, as the X-ray beam sweeps through the transverse plane of the patient 200.

Ideally, the sweep angle θ will be between 15° and 30°, as such an angle presents a good balance between patient X-ray dosage and image quality. However, in other applications, such as the imaging of other regions of the body, a different sweep angle θ, either wider or narrower, could equally be envisioned.

Furthermore, the rotation of the gantry 103 about the axis of rotation 203 permits bilateral imaging without disturbing the position of the patient; the gantry 103 rotates through 180° to reposition the X-ray sensor 101 and the X-ray source 102 to scan the patient 200 from the other side. In addition, the center of rotation 203 of the gantry 103 is displaced in the Z-direction so as to place the center of rotation 203 on the other side of the patient's head 200, and that the patient's head 200 remains in the vicinity of the sensor 101 (see FIG. 2).

This presents a considerable advantage over the cephalographic techniques presently known in the art, in that it produces two separate bilateral images, rather than one single image with superimposed anatomical figures.

Moreover, this is achieved with the same or a small increase in X-ray dosage relative to the cephalographic techniques known in the art, and with a greatly-reduced dosage relative to standard tomographic imaging techniques which irradiate the patient from many different angles, such as Cone Beam Computerized Tomography (CBCT).

By acquiring projections at two opposite angular extremes, separate images for left and right sides of the patient may be obtained: two half cephalometric images, with no superposition, are created with only twice the X-ray's dose of a classic 2D cephalogram.

Figure 5:
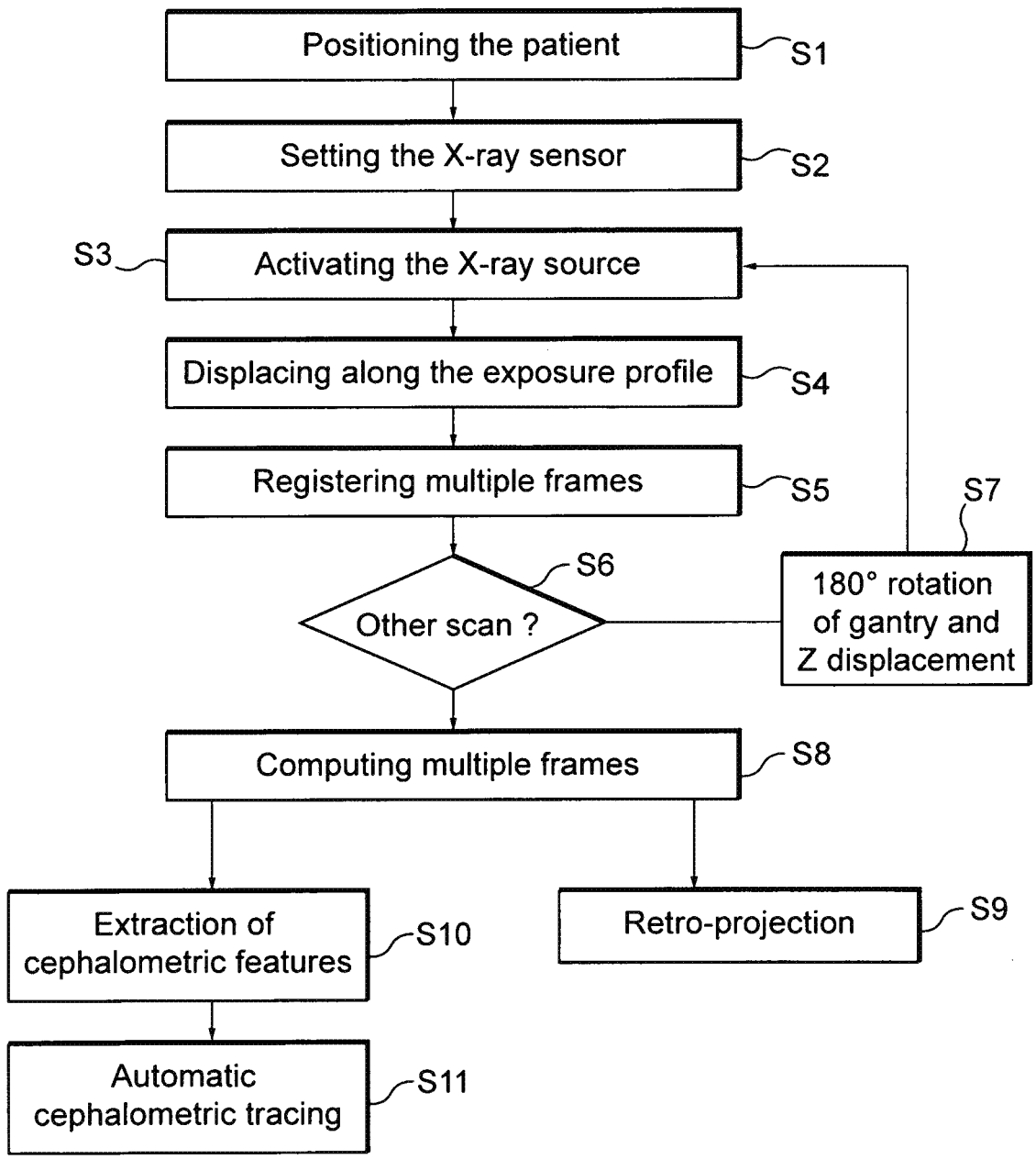
FIG. 5 is a flow chart that shows an exemplary method for performing a cephalometric image according to one embodiment of the invention.

Turning now to FIG. 5, an algorithm which implements the method according to an embodiment of the invention is discussed in further detail.

The method comprises a step for positioning S1 of the patient 200 between the X-ray source 102 and the X-ray sensor 101. This is ideally accomplished by the use of a headrest or brace as the patient holder 106 displayed in FIGS. 1A and 1B, so as to create a proper reference point upon which the data extracted during the scan can be constructed into an image.

Optionally, a setting step S2 is performed in order to set up the active area 300 of the X-ray sensor 101. As known in prior art, a collimator is used in front of the X-ray source 102 in order to adapt the X-ray beam to the active area 300 of the X-ray sensor 101.

As previously described, this active area is determined in order to have a long dimension m and a short dimension n with an aspect ratio m:n strictly inferior to 1.5.

Once the patient is positioned, there is an activating step S3 for activating the X-ray source, followed by a displacing step S4 for sweeping the X-ray beam across the patient. The displacing step S4 involves both synchronously translating and rotating the X-ray source 102 and X-ray sensor 101, thereby sweeping the beam across the patient as depicted in FIG. 2.

The multiple frames produced by the X-ray sensor 101 during the exposure of the skull are registered during a registering step S5.

Optionally, a test S6 is conducted in order to determine if an opposite scan is needed.

In the affirmative, a step S7 for repositioning the X-ray source 102 and X-ray sensor 101 is performed, in which the X-ray source 102 and sensor 101 are rotated through 180° about the patient 200, and the center of rotation 203 displaced in the Z-direction. In this way, the steps of activating S3, displacing S4 and registering S5 for a second scan of the patient 200 are achieved, which are performed in substantially the same way as described above with relation to steps S3 to S5.

Thus, in this embodiment the exposure profile comprises two separate substantially linear sections at two opposite angular extremes about the patient 200.

Once the scan(s) is (are) complete, the method reconstructs the data gathered by the X-ray sensor 101 into a useable image, for reconstructing three-dimensional volumetric data of the patient anatomy.

For this, the method comprises a step S8 of computing the multiple frames produced during at least part of the exposure. This computing step S8 involves applying a shift-and-add processing to reconstruct the image as a series of "slices," each containing a small portion of volumetric data describing the patient's anatomy.

Apart from tomosynthesis, other 3D reconstruction techniques can also be employed. The use of an iterative reconstruction algorithm such as SART (Statistical Algebraic Reconstruction Technique) or SIRT (Statistical Iterative Reconstruction Technique), or a technique like a Filtered Back Projection, to obtain the volumetric data opens up the possibility of obtaining an artifact-free volume with a very low x-ray dose. The Digital Cephalometric Tomosynthesis can be done with a dose between one and two times that of a classic 2D Cephalogram.

Generally, a single plane or the complete volume can be reconstructed using the Shift & Add, Filtered Back Projection, or Iterative techniques.

The Shift & Add algorithm is the fastest method, reconstructing a desired plane or set of planes according to the acquisition trajectory and desired anatomy. The Shift & Add algorithm does require the application of a de-blurring or enhancement filter to the reconstructed image, but is overall economic with computing resources.

The Filtered Back Projection technique is an approach similar to Shift & Add, but with the added possibility of obtaining a complete 3D volume. From this volume views along certain desired planes can then be extracted.

The iterative approaches (e.g. SIRT & SART) use some a priori information about the object, in particular, anatomical a priori information such as selected cranial measurements and/or the limits of the skull in space. The use of a priori information such as these can help compensate for limited angle problems, as well as help reduce the necessary x-ray dosage. However, iterative reconstruction methods are generally slower than other methods.

The reconstructed slices contain in focus imaging data belonging respectively to several depths of the imaged skull.

Figure 6:
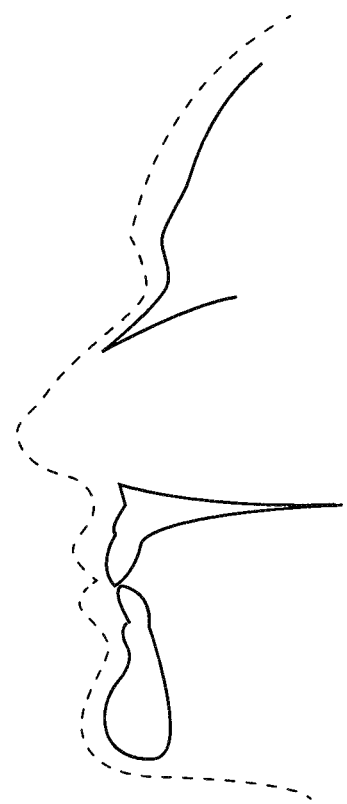
FIG. 6 is an example of the in focus features extracted from a slice on the zero sagittal plane of a human skull.

On the one hand, each slice can be used for the extraction of some cephalometric features. As depicted in FIG. 6, the in focus features extracted from a slice on the mid-sagittal plane of a human skull may be obtained.

Moreover, the extracted features through different depths can be put together to provide a cephalometric image.

Figure 7:
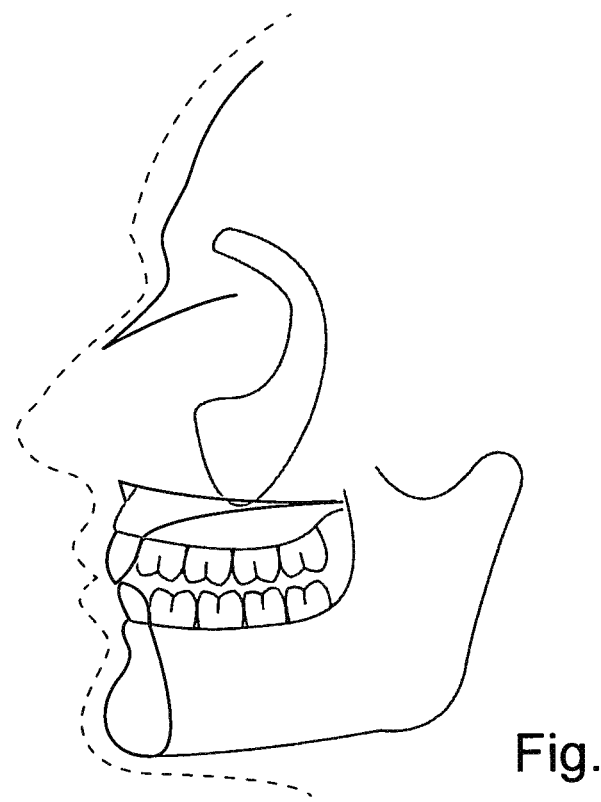
FIG. 7 is an example of the superimposition of the in focus features extracted from all slices belonging to a left part of a human skull.

As shown in FIG. 7, the superimposition of at least some of the in focus features extracted from all slices belonging to a left part of a human skull provides an half cephalometric image for the left side of the patient.

Such a reconstruction is particularly advantageous, in that unlike the methods known in the art, the reconstruction is not limited to a narrow focal trough in which the image is clear and undistorted, but rather each aspect of the patient's anatomy is represented by the slice in which that aspect is displayed with the highest fidelity and resolution. Such a method will ultimately produce an accurate, three-dimensional model of the patient's anatomy while simultaneously vastly reducing or minimizing X-ray dosage.

A consequence of this is that a great deal of other, more conventional images can be simulated through simple data processing methods, based on the model produced in the step S8 for reconstructing the 3D volumetric data.

For instance, simulated left and right 2D lateral images, either separate or superimposed, can be constructed by passing the 3D model through a step S9 for retro-projecting, i.e. simulating a standard cephalogram as produced by a "ceph arm"-equipped imaging system through known rendering techniques such as cone beam or parallel geometry projection.

Such a retro-projection might be calibrated to produce a simulated retro-projection distance of between 1.5 m and 4 m, so as to best simulate the images produced by current imaging systems; however it will be understood that other projection distances might also be advantageous in other applications, and that the method of the present invention can easily be so adapted. An infinite projection distance is particularly advantageous, in that it corresponds to a parallel beam projection.

The synthetized 2D cephalogram looks like a standard cephalogram as obtained with a X-ray sensor located on a cephalometric arm of 1.50 m or more related to the position of the X-ray source.

Producing a panoramic image of the mandible and dentition may also be envisioned, performed in a similar way using other, appropriate rendering methods.

These extracted, simulated images can in themselves have important diagnostic and therapeutic uses.

For instance, by extracting the relevant cephalometric features from the 3D model and/or 2D images, and identifying them on said 2D lateral images in an extraction step S10, a cephalometric tracing can be produced at an automatic cephalometric tracing step S11. Such a cephalometric tracing yields valuable diagnostic and therapeutic data, and is much easier and faster to produce than the plaster-molding methods presently employed.

Figure 8:
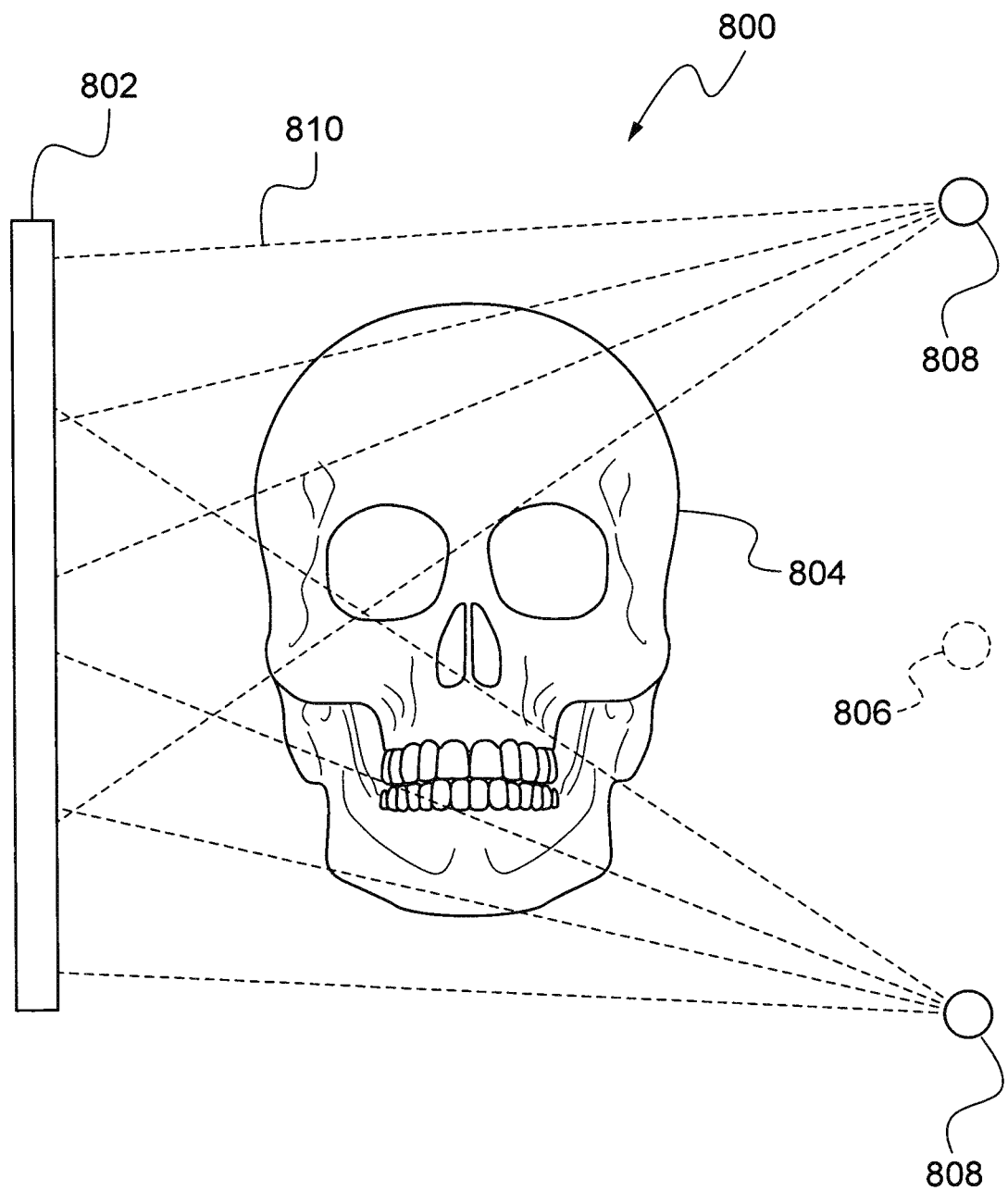
FIG. 8 is a schematic representation of a scan performed in another embodiment of the invention.

Finally, FIG. 8 depicts a possible variant embodiment of the invention.

In FIG. 8, a scanning apparatus 800 comprises a sensor 802 which is relatively large compared to the ones of previously-discussed embodiments. Ideally, the sensor is approximately 210 mm by 150 mm, but in any event with an aspect ratio lower than 1.5:1.

With such a large sensor it is possible to scan a patient's head 804 in one pass, by using a single x-ray source 806 dispersing at a wide angle. However, this may create distortions and artifacts in the reconstructed image.

To resolve this, the patient's head 804 is scanned with an X-ray source 808 at several discrete positions, with only a portion of the sensor 802 is illuminated in each scan. Here, the scan is performed with the X-ray source 808 first in an upper position, and again with the same X-ray source 808 displaced into a lower position. Other embodiments may envision additional scans at intermediate positions, as appropriate.

The x-rays 810 are emitted by the x-ray source 808 at a relatively narrow angle, such that only a portion of the sensor 802 is illuminated with each scan. However, the images produced by the several scans may be stitched together using known techniques. This creates a large, high-resolution reconstruction with low distortion and only a minimal increase in X-ray dosage relative to other embodiments.

It should be understood that various changes and modifications to the presently preferred embodiments described herein will be apparent to those skilled in the art. Such changes and modifications can be made without departing from the spirit and scope of the present invention and without diminishing its attendant advantages. In addition, while a particular feature of the invention can have been disclosed with respect to one of several implementations, such feature can be combined with one or more other features of the other implementations as can be desired and advantageous for any given or particular function. It is therefore intended that such changes and modifications be covered by the appended claims.

The invention claimed is:

1. A method for creating a cephalometric image of at least part of a human skull using a cone beam computed tomography extra-oral dental imaging system having a conical shape x-ray beam and no cephalometric arm, said system comprising:
 an X-ray source for producing the conical shape x-ray beam, said conical shape x-ray beam being used for irradiating a human skull to be imaged;
 an imaging device suitable for producing multiple frames during at least part of an exposure of said human skull, said imaging device being positioned in a position relative to said X-ray source absent use of a cephalometric arm;
 a manipulator for displacing the imaging device along an exposure profile between multiple frames during said at least part of the exposure of said human skull to be imaged, the manipulator permitting the movement of the X-ray source and the imaging device via selective translation and selective rotation,
 wherein the method comprises the steps of:
  setting said imaging device with an active area having a long dimension m and a short dimension n, wherein the aspect ratio m:n is less than 1.5;
  synchronously displacing the X-ray source and the imaging device along said exposure profile, said exposure profile comprising at least one substantially linear section wherein said X-ray source and said imaging device are translated along said substantially linear section while rotating in the same rotational direction; and
  registering said multiple frames produced by the imaging device during the exposure of said human skull to be imaged;
  wherein the method is operable to produce two separate bilateral cephalometric images without superimposed anatomical figures, said separate bilateral cephalometric images being stitchable together to form a single cephalometric image.

2. A method according to claim 1, wherein the at least one substantially linear section of the exposure profile is oriented parallel to a mid-sagittal plane or a coronal plane, or angled to said mid-sagittal plane.

3. A method according to claim 1, wherein said exposure profile comprises at least two separate substantially linear sections at two opposite angular extremes about said human skull to be imaged.

4. A method according to claim 1, wherein said short dimension n of the active area of the imaging device extends along said at least one substantially linear section during the exposure of said human skull.

5. A method according to claim 1, wherein the angular range ($\theta$) of the rotational movement of the imaging device and the X-ray source is between 15 degrees and 30 degrees.

6. A method according to claim 1, wherein the X-ray source is displaced along a trajectory having a curvature directed towards said human skull, and the imaging device is displaced along a trajectory having a curvature directed away from said human skull.

7. A method according to claim 1, wherein the length of said at least one substantially linear section is comprised between 70 and 250 mm.

8. A method according to claim 1, wherein said aspect ratio m:n is less than 1.2.

9. A method according to claim 1, wherein the long dimension m of said active area is equal to 140 mm and the short dimension n of said active area is equal to 120 mm.

10. A method according to claim 1, wherein the long dimension m of said active area is equal to 210 mm and the short dimension n of said active area is equal to 150 mm.

11. A method according to claim 1, wherein the method further comprises a step of computing said multiple frames produced during at least one part of the exposure:
 by a shift-and-add processing, thereby reconstructing at least one slice; or
 by a volumetric approach, thereby reconstructing a three-dimensional volume and subsequently extracting at least one slice from this volume;
 wherein said at least one slice includes in-focus imaging data belonging respectively to at least one depth of said human skull to be imaged.

12. The method according to claim 11, wherein the volumetric approach is selected from a Statistical Algebraic Reconstruction Technique (SART), a Statistical Iterative Reconstruction Technique (SIRT), or a Filtered Back Projection Technique.

13. A method according to claim 11, wherein said several slices are reconstructed and combined to give a separate linear projection for each of the left and right sides of said human skull.

14. A method according to claim 11, wherein said several slices are reconstructed and retro projected to a distance superior to 1.50 meters, and preferably superior to 4 meters, on a cone beam or parallel geometry so as to create a synthesized 2D cephalogram of said human skull.

15. A method according to claim 1, wherein the method further comprises a step of using each reconstructed slice for the extraction of cephalometric features.

16. A method according to claim 15, wherein the method further comprises a step of automatic cephalometric tracing, wherein said extracted cephalometric features of each slice are put together.

17. A cone beam extra-oral dental imaging system for creating a cephalometric image of at least part of a human skull without the use of a cephalometric arm and without superposition of images, said system comprising:

an X-ray source configured to produce an x-ray beam having a cone shape and to irradiate a human skull to be imaged;

an imaging device suitable for producing multiple frames during at least part of an exposure of said human skull, said imaging device being located relative to said X-ray source at a location normally used for producing panoramic images or computed tomography images; and a manipulator for displacing the imaging device along an exposure profile between multiple frames during said at least part of the exposure of said human skull, the manipulator permitting the movement of the X-ray source and the imaging device in unison by selective translation and selective rotation, wherein said imaging device has an active area having a long dimension m and a short dimension n, wherein the aspect ratio m:n is less than 1.5;

wherein said manipulator synchronously displaces the X-ray source and the imaging device along said exposure profile, said exposure profile comprising at least one substantially linear section wherein said X-ray source and said imaging device are translated while rotating in the same direction; and wherein said imaging system is configured to produce the cephalographic image from multiple frames captured from the active area during the displacement of the X-ray source and the imaging device along said exposure profile.

18. The system according to claim 17, wherein said manipulator is configured to rotate the X-ray source and the imaging device in unison through an angle having an angular measure between zero degrees and thirty degrees during displacement of the X-ray source and the imaging device along the exposure profile.

19. The system according to claim 17, wherein the exposure profile is configured such that the profile of the patient is irradiated and imaged with an almost perpendicular angle of incidence during operation.

20. The system according to claim 17, wherein the exposure profile is configured such that during operation of the system, the curvature of the trajectory of the X-ray source is directed towards the patient and the curvature of the trajectory of the imaging device is directed away from the patient.

21. The system according to claim 17, wherein the exposure profile is configured such that during operation of the system, there exists an instantaneous center of rotation that is located on the other side of the imaging device from the X-ray source.

22. The system according to claim 17, wherein the exposure profile includes at least one substantially linear section oriented parallel to a mid-sagittal plane or a coronal plane, or angled to said mid-sagittal plane.

\* \* \* \* \*